United States Patent [19]

Hiraoka

[11] Patent Number: 5,476,523
[45] Date of Patent: Dec. 19, 1995

[54] MOSS SEEDLING AND METHOD OF PRODUCING DENSE MOSS MAT THEREFROM

[75] Inventor: Shozaburoh Hiraoka, Kawasaki, Japan

[73] Assignee: The Hiraoka Environmental Science Laboratory, Kanagawa, Japan

[21] Appl. No.: 125,207

[22] Filed: Sep. 23, 1993

[51] Int. Cl.⁶ .............................. A01H 4/00; A01H 11/00; A01G 1/00; A01G 7/00
[52] U.S. Cl. .................... 47/58; 435/240.45; 435/240.49
[58] Field of Search .................... 800/200; 435/240.4, 435/240.45, 240.48, 240.49, 240.54; 47/58.25, 58

[56] References Cited

FOREIGN PATENT DOCUMENTS

| 249772 | 5/1987 | European Pat. Off. . |
| 281374 | 3/1988 | European Pat. Off. . |
| 1401665 | 5/1972 | United Kingdom . |

OTHER PUBLICATIONS

Huxley et al., eds. 1992. The New Royal Horticultural Society Dictionary of Gardening. p. 405.
Bopp et al. 1984. In Cell Culture and Somatic Cell Genetics of Plants, vol. 1, Vasil, ed. Ch. 12:96–105.
Dodds et al. 1984. Experiments in Plant Tissue Culture. Ch. 1: 1–9.
Menon et al. 1990. In Bryophyte Development: Physiology and Biochemistry, Ch. 10: 191–207.
Everett, ed. 1960. New Illustrated Encyclopedia of Gardening. Vol. 7: 1189. Greystone Press, N.Y.
Scandrett et al. 1989. Journal of Ecology. 77:838–852.
Proctor. 1984. In the Experimental Biology of Bryophytes. pp. 21–22.
Kagaku, Gendai, "Plant Biotechnology" Modern Chemistry, No. 5, 1986.
Katoh, Kenji, "Isolation and maintenance of Callus and Cell Suspension Cultures and Bryophytes.", Methods in Bryology, 1988, pp. 99–105.

*Primary Examiner*—David T. Fox
*Assistant Examiner*—Erich E. Veitenheimer
*Attorney, Agent, or Firm*—Browdy and Neimark

[57] ABSTRACT

Plant tissues of mosses such as cut tissue pieces, gametophores, calluses, protonemata, spores, gemmae, subterranean stems or rhizoids are purely cultured in a culture medium to generate seedlings (cultigen) corresponding to plumules, and the seedlings are sown onto a nursery at a desired colony density, followed by appropriate caring.

3 Claims, No Drawings

MOSS SEEDLING AND METHOD OF PRODUCING DENSE MOSS MAT THEREFROM

BACKGROUND OF THE INVENTION

The present invention relates to a seedling of moss (bryophyte) usable as a cultigen and a method of producing a dense moss mat by using such seedlings, and more particularly to a moss seedling easily cultivated to a dense colony, and a method of easily producing a dense colony of mosses from the seedlings in a short period of time.

It has been traditionally preferred that the soil of a garden be covered with various plants to create a natural beauty. A typical example of such soil-covering plants is grass, but mosses are much preferred to grass in the Japanese garden.

Though there are mosses tolerant of a direct sunshine, some species of mosses are weakened by exposure to direct sunshine, not adapted for a fertile soil and grow by absorbing moisture in the air through their leaves. Accordingly, attention has recently been paid to the mosses for applications not only in the conventional moss garden, but also in roof garden, etc. Also, they are planted outdoors in hotels, Japanese inns, etc. to create the traditional Japanese atmosphere.

The beauty of the mosses does not originate from flowers unlike floral plants, but it is derived from the dense colony consisting of a large number of individual mosses. However, since the biology of the mosses has been still mostly unknown, it is difficult to cultivate the mosses on a large scale by a usual garden cultivation method. For instance, the cultivation of *Racomitrium canescens* and *Dicranum japonicum* can actually be conducted only by highly skilled gardeners.

The conventional cultivation methods of the mosses are generally classified into a transplantation method and a regeneration method.

The transplantation method comprises collecting a desired moss with a soil on which it is growing, and planting it on a desired place. This method is, however, disadvantageous in that it is not suitable for plantating of the moss in a wide area.

The regeneration method, which utilizes the strong regenerating nature of the mosses, may be classified into a cuttage method, a sowing method, a root separation method, etc., and the sowing method is most commonly conducted. In the sowing method, the mat of the moss colony collected in mountains, fields, etc. is separated or divided into each moss plant or small pieces of the moss plant, and planted on a nursery, causing plumules to grow from the separated moss plants or pieces of the divided moss plants, so that they can be multiplied.

However, the sowing method is disadvantageous in that all divided moss plants are rarely regenerated to have plumules, and that even in a case where all divided moss plants are regenerated, it is impossible to sow the divided pieces of the moss plants at a density corresponding to that of the moss colony, resulting in a sparsely grown moss colony at the initial stage. In order to have a dense moss colony, one must wait until lateral buds or gemmae have grown to full size from the subterranean stems. Such growth of the lateral buds or gemmae usually takes several years, during which the moss colony should be well nurtured. Further, in the nursery on a cultivation soil of 30 cm×60 cm, one can prepare only two to four cases of the nursery a day, if he works 7 hours a day to sow the divided pieces of the moss plants one by one at a constant interval. This is extremely low efficiency. On the other hand, there are some mosses such as Polytrichum, etc. which grow so rapidly that they can form a colony in about one year. Such mosses, however, have so short a life span as plants that they die in a short period of time. Because of these reasons, moss gardens, moss pots, etc. are extremely expensive.

Since mosses such as Sphagnum have not only good resistance to fungi but also an excellent water retention ability, they are used to cover soils of pots for expensive and weak floral plants and trees such as orchids, bonsai (dwarfed tree), etc., in order to protect the weak plants and trees from harmful fungi and prevent them from extreme dryness. However, if these mosses are collected in the forests and the mountains excessively, the water retention ability of the forests and the mountains would become so low that landslide, flooding, etc. are likely to take place. Further, once the moss colony is removed from the surface of the soil or rock, it takes many years in a natural environment until the surface of the soil or rock is covered by a moss colony again. Thus, to protect the nature of the earth, it is important to keep the moss colony from being excessively removed from the surface of the soil or rock.

SUMMARY OF THE INVENTION

Accordingly, an object of the present invention is to provide a moss seedling which can easily grow to a dense moss colony.

Another object of the present invention is to provide a method of producing a moss seedling from which a dense moss colony can easily be formed in a short period of time.

As a result of intense research in view of the above object, the inventor has found that by multiplying plant tissues of mosses such as gametophores, protonemata, spores, calluses, etc. by a pure culture in a culture tank to form seedlings which correspond to plumules, and sowing the seedlings onto a nursery at a desired colony density, a dense moss colony can be formed in a short period of time. The present invention has been completed based on this finding.

Thus, the moss seedling according to the present invention is obtained by pure culture of the plant tissues of the mosses.

The method of producing a dense mat of a moss colony according to the present invention comprises the steps of (a) purely culturing the plant tissues of the moss in a culture medium to generate seedlings thereof, (b) sowing the seedlings onto a nursery at a desired colony density and (c) caring, the seedlings so that they mature to full size.

DESCRIPTION OF THE PREFERRED EMBODIMENTS

[A] Moss seedlings

The mosses (bryophytes) to be cultured to produce seedlings (cultigen) in the present invention generally include musci (Bryopsida), hepaticae (Hepaticopsida) and anthocerotae (Anthocerotopsida). The Bryopsida generally include Sphagnidae, Andreaeidae, Bryidae (Polytrichales, Dicranales, Eubryales, etc.), etc. The Hepaticae generally include Marchantiales, Metzgeriales, Jungermanniales, etc. The anthocerotae generally include anthocerotaceae, etc.

Representative mosses used for moss gardens, moss pots, coverings for flower pots, etc. are Dicranales, Racomitrium, Leucobryum and Bryum as well as Sphagnaceae, etc.

The seedlings of such mosses will be described below.

First, the plants or spores of mosses are collected in fields or mountains, and the plant tissues of the mosses are multiplied by pure culture to form seedlings. Alternatively, the plant tissues of the mosses may be subjected to pure culture for differentiation to seedlings and then multiplied.

The next point of the present invention is to cultivate the seedlings to form a dense mat of a moss colony. The seedlings to be cultured in the present invention correspond to the plumules. Depending on the plant tissues to be cultured, the seedlings may not be clearly confirmed as the plumules, or the seedlings may be identified only as small projections in the plants. Even in such cases, almost 100% of the plumules can germinate and grow in the method of the present invention.

The plant tissues of the mosses to be cultured may be gametophores, tissue pieces, spores, gemmae, subterranean stems, rhizoids, protonemata, etc. Also, calluses derived from these plant tissues may be cultured.

Which forms of plant tissues are most suitable for pure culture and what courses of culture are most suitable depend on the species of the mosses. Further, in some cases the plant tissues may be treated to derive calluses, which may be then converted to the seedlings such as plumules.

Accordingly, the derivation and culture of the moss seedlings may be conducted by the following methods (A)–(L):

(A) Gametophores→Seedlings.

(B) Gametophores→Calluses→Seedlings.

(C) Gametophores→Protonemata→Seedlings.

(D) Spores→Protonemata→Seedlings.

(E) Spores→Protonemata→Calluses→Seedlings.

(F) Gemmae→Seedlings.

(G) Gemmae→Calluses→Seedlings.

(H) Tissue pieces→Seedlings.

(I) Tissue pieces→Calluses→Seedlings.

(J) Protonemata→Seedlings.

(K) Subterranean stems→Seedlings.

(L) Rhizoids→Seedlings.

The above culture and differentiation of the plant tissues are conducted in a culture medium which may be a solid culture medium or a liquid culture medium. For instance, various Murashige-Skoog modified culture media (MS modified culture media) mentioned below may be selected depending on the plant forms of the mosses to be cultured and the desired forms of the cultured mosses, and if necessary, plant growth control substances such as kinetin, benzyladenine, indole-3-acetic acid, 2,4-dichlorophenoxyacetic acid (2,4-D), etc. may be added.

In general, the plant tissues of the mosses are likely to be converted to calluses in a culture medium having a high concentration (2 weight % or higher) of monosaccharide such as glucose or disaccharide, and the calluses are easily converted to the seedlings in a culture medium having a low concentration (0.4 weight % or lower) of sugar.

The above methods (A)–(L) will be explained in the case of using the MS modified culture media having compositions consisting of Solution Nos. 1–3 (solvent: distilled water) described below; sugars such as glucose; vitamins; organic acids, inorganic acids or their salts; and distilled water.

Solution No. 1

| | |
|---|---|
| Calcium chloride dihydrate | 4,400 mg/liter, |
| Magnesium sulfate heptahydrate | 3,700 mg/liter, |
| Manganese sulfate tetra- to penta-hydrate | 223 mg/liter, |

-continued

| | |
|---|---|
| Boric acid | 62 mg/liter, |
| Zinc sulfate heptahydrate | 107 mg/liter, |
| Sodium molybdenate dihydrate | 2.5 mg/liter, |
| Copper sulfate pentahydrate | 0.25 mg/liter, |
| Cobalt chloride hexahydrate | 0.25 mg/liter, and |
| Potassium iodide | 8.3 mg/liter. |

Solution No. 2

| | |
|---|---|
| Potassium dihydrogenphosphate (KH$_2$PO$_4$) | 42.5 mg/liter. |

Solution No. 3

| | |
|---|---|
| Myo-inositol | 10,000 mg/liter, |
| Nicotinic acid | 50 mg/liter, |
| Pyridoxine-hydrochloric acid | 50 mg/liter, and |
| Thiamine.hydrochloric acid | 10 mg/liter. |

Compositions of various MS modified culture media

NA-MS culture medium

| | |
|---|---|
| Solution No. 1 | 100 ml/liter, |
| Solution No. 2 | 4 ml/liter, |
| Solution No. 3 | 10 ml/liter, |
| Glucose | 20 g/liter, |
| Potassium nitrate | 4 g/liter, |
| EDTA*.Disodium | 47 mg/liter, and |
| Iron sulfate heptahydrate | 27.8 mg/liter. |
| pH = about 5.8. | |

AS-MS culture medium

| | |
|---|---|
| Solution No. 1 | 100 ml/liter, |
| Solution No. 2 | 4 ml/liter, |
| Solution No. 3 | 10 ml/liter, |
| Glucose | 20 g/liter, |
| EDTA*.Disodium | 47 mg/liter, |
| Iron sulfate heptahydrate | 27.8 mg/liter, |
| Ammonium chloride | 44 mM, and |
| Sodium succinate or sodium fumarate | 33 mM. |
| pH = about 5.8. | |

ANA-MS culture medium

| | |
|---|---|
| Solution No. 1 | 100 ml/liter, |
| Solution No. 2 | 4 ml/liter, |
| Potassium nitrate | 4 g/liter, |
| EDTA*.Disodium | 47 mg/liter, and |
| Iron sulfate heptahydrate | 27.8 mg/liter. |
| pH = about 5.8. | |

AAS-MS culture medium

| | |
|---|---|
| Solution No. 1 | 100 ml/liter, |
| Solution No. 2 | 4 ml/liter, |
| EDTA*.Disodium | 47 mg/liter, |
| Iron sulfate heptahydrate | 27.8 mg/liter, |
| Ammonium chloride | 44 mM, and |
| Sodium succinate or sodium fumarate | 33 mM. |
| pH = about 5.8. | |

MSF culture medium

| | |
|---|---|
| Solution No. 1 | 10 ml/liter, |
| Solution No. 2 | 0.4 ml/liter, |
| Solution No. 3 | 1 ml/liter, |
| Glucose | 2 g/liter, |
| Potassium nitrate | 0.4 g/liter, |
| EDTA*.Disodium | 4.7 mg/liter, |
| Iron sulfate heptahydrate | 2.78 mg/liter, |
| Ammonium chloride | 20 mM, and |
| Sodium succinate or sodium fumarate | 15 mM. |
| pH = about 5.8. | |

Culture Method (A) Gametophores → Seedlings (1) Sterilization

Note:
*Ethylenediaminetetraacetic acid.

The gametophores are cut to about 1–10 mm, and cultured on a 1/5 (diluted 5 times) NA-MS culture medium (solidified with agar; Gelrite®, etc.) at 20°–25° C. while illuminating a light of about 1000–3000 lux. After removing portions infected with fungi, etc., the culture operation of the gametophores are repeated several times to produce sterilized gametophores.

The above sterilization operation is conducted, for instance, by washing the gametophores (one type of the plant tissues of the mosses to be sterilized) with a solution (concentration: about 0.1–0.5 volume %) of a nonionic surfactant such as polyoxyethylene sorbitan monolaurate (tradename: Tween 20), polyoxyethylene sorbitan monooleate (tradename: Tween 80), etc. or a cationic surfactant such as benzalkonium chloride, etc. for 40–60 seconds by means of a stainless steel syringe holder, etc.; sterilizing the gametophores with a solution of 0.5–1 volume % of sodium hypochlorite, etc.; and immediately fully washing the gametophores with germ-free distilled water. The gametophores thus sterilized are cultured. If it is found that there are portions in the gametophores infected with the fungi, those portions should be removed, and the above sterilization operation should be repeated until infected portions disappear.

(2) Derivation and multiplication of seedlings

The resulting, sterilized gametophores are cultured in a 1/5 ANA-MS culture medium (liquid, photoautotrophic culture medium) in which carbon dioxide is enriched to 1%, or a 1/5 NA-MS culture medium (liquid) containing 0.1–10 p.M of a growth control substance at 20°–25° C. for 10–30 days while illuminating a light of about 1000–3000 lux. As a result, the gametophores give rise to seedlings.

Incidentally, when the growth control substance is added to the culture medium, the derived seedlings are taken out from the culture medium after 3–10 days, fully washed with the 1/5 NA-MS culture medium, and then introduced into the 1/5 NA-MS culture medium containing no growth control substance to continue the culture of the seedlings.

The multiplication of the seedlings can be efficiently conducted, for instance, by pouring the gametophores into a container such as a conical flask, etc. together with a culture medium, and shaking it at 110–120 rpm/min. Alternatively, the gametophores can be poured into a container such as a shallow flask, etc. together with a culture medium to conduct a suspension culture. In the suspension culture, the seedlings derived from the ametophores are cut one after another by shaking and each divided piece of the seedlings grows. As a result, the sterilized seedlings can be cultured on a large scale.

The seedlings thus cultured are collected from the culture medium, fully washed with a sterilized distilled water to completely remove the culture medium, and then dried at 25°–35° C. while blowing air, or under a sunshine, or freeze-dried at a temperature between −20° C. and −5° C. Thus, moss seedlings can be obtained in a dry state. The dried seedlings thus obtained can be kept alive in storage for a long period of time (more than 1 year). Alternatively, the moss seedlings dispersed in the culture medium can be retained in a bottle. After multiplication for 4–8 weeks, the number of the seedlings (cultigen) can be as many as 100–150 times the number of the divided gametophores.

The mosses suitable for this procedure (A) are as follows:

(a) Bryopsida
Atrichum, Fissidens, Blindia, Brachydontium, Aongstroemia, Brothera, Bruchia, Bryohumbertia, Campylopodium, Campylopus, Cynodontium, Dichodontium, Dicranella, Dicranodontium, Dicranoloma, Dicranoweisia, Dicranum, Kiaeria, Leucoloma, Oncophorus, Oreas, Oreoweisia, Paraleucobryum, Rhabdoweisia, Trematodon, Leucobryum, Chenia, Desmatodon, Dialytrichla, Didymodon, Eucladium, Gymnostomum, Hydrogonium, Hymenostylium, Hyophila, Leptodontium, Luislerella, Molendoa, Oxystegus, Phascum, Portia, Pseudosymblepharis, Scopelophila, Streblotrichum, Timmiella, Tortella, Tortula, Trichostomun, Tuerckheimia, Weissia, Racomitrium, Rhodobryum, Cinclidium, Mnium, Orthomnion, Aulacomnium, Pyrrhobryum, Climacium, Thamnobryum, Dolichomitra, Hookeria, Thamniopsis, Cyathophorella, Hypopterygium, Thudium, Homalothecium, Hypnum, etc.

(b) Hepaticopsida
Haplomitrium, Ricciocarpus, etc.

(B) Gametophores→Calluses→Seedlings (1) Sterilization
The same as in (A).

(2) Derivation of calluses
The gametophores sterilized in the above step (1) are cultured on a 1/5 AS-MS culture medium (solid) in which the concentration of glucose is controlled to 4–8 weight %, or on an MFS culture medium (solid) at 20°–25° C. for 30–60 days while illuminating a light of about 1500–2000 lux. As a result, the gametophores give rise to calluses.

(3) Multiplication of calluses
The derived calluses are multiplied in an AS-MS culture medium (liquid) in which the concentration of glucose is controlled to 2–4 weight %, or in an AAS-MS culture medium (liquid, photoautotrophic culture medium) in which carbon dioxide is enriched to 1%, at 20°–25° C. for 15–20 days while shaking at 110–120 rpm/min and illuminating a light of about 1000–3000 lux. After multiplication for 45–90 days, the number of the seedlings (cultigen) can be as many as 100–150 times the number of the divided gametophores.

The multiplied calluses may be stored in an AS-MS culture medium in which the concentration of glucose is controlled to 2 weight %.

(4) Derivation of seedlings
The resulting calluses are cultured in a 1/5 ANA-MS culture medium (liquid, photoautotrophic culture medium) in which carbon dioxide is enriched to 1%, or a 1/5 NA-MS culture medium (liquid) at 20°–25° C. for 30–60 days while shaking at 110–120 rpm/min and illuminating a light of about 1000–3000 lux. As a result, the calluses give rise to seedlings. The seedlings thus obtained may be sown and stored in the same manner as in the above procedure (A). After multiplication for 8–15 weeks, the number of the seedlings (cultigen) can be as many as 100–150 times the number of the divided gametophores.

This procedure is suitable for the mosses which can grow fast through their calluses or those which can be well stored in the state of calluses. Representatives of such mosses are as follows:

(a) Bryopsida
Bartramia, Barbttla, Polytrichum, Atrichum, Sphagnum, etc.

(b) Hepaticopsida
Marchantia, Jungermannia, Plagiochila, etc.

(C) Gametophores→Protonemata→Seedlings (1) Sterilization
The same as in (A).

(2) Derivation of protonemata
The gametophores sterilized in the above step (1) are cultured on a 1/5 ANA-MS culture medium (solid) at 20°–25° C. for 5–10 days while illuminating a light of about 1000–3000 lux. As a result, the gametophores give rise to protonemata.

(3) Derivation and multiplication of seedlings

The derived gametophores are multiplied in a 1/5 ANA-MS culture medium (liquid, photoautotrophic culture medium) in which carbon dioxide is enriched to 1%, or in a 1/5 NA-MS culture medium (liquid), at 20°–25° C. for 30–60 days while shaking at 110–120 rpm/min and illuminating a light of about 1000–3000 lux. As a result, the protonemata give rise to seedlings. After multiplication for 5–10 weeks, the number of the seedlings (cultigen) can be as many as 100–150 times the number of the divided gametophores.

The multiplied seedlings may be stored in the same manner as in the above procedure (A).

This procedure is suitable for the mosses which can grow fast through their protonemata. Representatives of such mosses are as follows:

(a) Bryopsida
Ceratodon, Distichium, Ditrichum, Bartramia, Piagiopus, etc.

(b) Hepaticopsida
Scapania, Marchantia, Jungermannia, etc.

(D) Spores→Protonemata→Seedlings
(1) Sterilization

Spores (calyptrae, if any, are removed from capsules) are sterilized in the same manner as in the above procedure (A).

(2) Derivation of protonemata

The spores sterilized in the above step (1) are cultured on a 1/5 ANA-MS culture medium (solid) at 20°–25° C. for 10–15 days while illuminating a light of about 1000–3000 lux. As a result, the spores give rise to protonemata.

(3) Derivation and multiplication of seedlings

The same as in (C).

The multiplied seedlings may be stored in the same manner as in the above procedure (A).

This procedure is suitable for the mosses which can grow fast through their spores instead of gametophores. Representatives of such mosses are as follows:

(a) Bryopsida
Atrichum, Pogonatum, Polytrichastrum, Polytrichum, Dicranum, Leucobryum, Racomitrittm, Funaria, Physcomitrium, Gymnostomiella, Oedipodittm, Splachnum, Tayloria, Tetraplodon, Anomobryum, Brachymenium, Bryum, Epipterygium, Leptobryum, Mielichhoferia, Plagiobryttm, Pohlia, Pseudobryum, Rhizomnium, Pyrrhobryum, Bartramia, Breutelia, Fleischerobryum, Philonotis, Plagiothecium, Cteniditum, Ectropothecium, Hypnum, etc.

(b) Hepaticopsida
Plagiochila, Frullania, Bazzania, etc.

(E) Spores→Protonemata→Calluses→Seedlings
(1) Sterilization

Spores (calyptrae, if any, are removed from capsules) are sterilized in the same manner as in the above procedure (A).

(2) Derivation of protonemata

The same as in (D).

(3) Derivation of calluses

The protonemata obtained in the above step (2) are cultured on a 1/5 AS-MS culture medium (solid) in which the concentration of glucose is controlled to 4–8 weight %, or on an MFS culture medium (solid) at 20°–25° C. for 30–60 days while illuminating a light of about 1500–2000 lux. As a result, the protonemata give rise to calluses.

(4) Multiplication of calluses

The calluses thus derived can be multiplied in the same manner as in the above procedure (B).

(5) Derivation and multiplication of seedlings

The same as in (B).

The multiplied seedlings may be stored in the same manner as in the above procedure (A).

This procedure is suitable for the mosses which can grow fast through their calluses or those which can be well stored in the state of calluses. Representatives of such mosses are as follows:

(a) Bryopsida
Sphagnum, Barbula, Trachycystis, Bartramia, etc.

(b) Hepaticopsida
Plagiochila, Radula, Bazzania, etc.

(F) Gemmae→Seedlings
(1) Sterilization

Gemmae are cut into about 1–10 mm and sterilized in the same manner as in the above procedure (A).

(2) Multiplication of gemmae

The sterilized gemmac are multiplied on a 1/5 NA-MS culture medium (solid) at 20°–25° C. for 10–15 days while illuminating a light of about 1000–3000 lux.

(3) Derivation and multiplication of seedlings

The gemmac obtained in the above step (2) are cultured in a 1/5 ANA-MS culture medium (liquid, photoautotrophic culture medium) in which carbon dioxide is enriched to 1%, or in a 1/5 NA-MS culture medium (liquid) containing 0.1–10 gM of a growth control substance, at 20°–25° C. for 15–30 days while shaking at 110–120 rpm/min and illuminating a light of about 1000–3000 lux. As a result, the gemmac give rise to seedlings. After multiplication for 4–8 weeks, the number of the seedlings (cultigen) can be as many as 100–150 times the number of the divided gemmae.

The multiplied seedlings may be stored in the same manner as in the above procedure (A).

This procedure is suitable for the mosses which can grow fast through their gemmae. Representatives of such mosses are as follows:

(a) Bryopsida
Pohlia, Tetrodontium, Dicranum, Trachycystis, etc.

(b) Hepaticopsida
Marchantia, Metzgeria, Conocephalum, etc.

(G) Gemmae→Calluses→Seedlings
(1) Sterilization

The same as in (F).

(2) Derivation of calluses

The gemmae sterilized in the above step (1) are cultured on a 1/5 AS-MS culture medium (solid) in which the concentration of glucose is controlled to 4–8 weight %, or on an MFS culture medium (solid) at 20°–25° C. for 30–60 days while illuminating a light of about 1500–2000 lux. As a result, the gemmae give rise to calluses.

(3) Multiplication of calluses

The calluses thus derived can be multiplied and stored in the same manner as in the above procedure (B).

(4) Derivation and multiplication of seedlings

The calluses can be converted to seedlings and multiplied in the same manner as in the above procedure (B). After multiplication for 8–17 weeks, the number of the seedlings (cultigen) can be as many as 100–150 times the number of the divided gemmae. The multiplied seedlings may be stored in the same manner as in the above procedure (A).

This procedure is suitable for the mosses which can grow fast through their calluses or those which can be well stored in the state of calluses. Representatives of such mosses are as follows:

(a) Bryopsida
Hyophila, Pohlia, Pseudotaxiphyllum, Pylaisiadelpha, etc.

(b) Hepaticopsida
Marchantia, Metzgeria, Cololejeunea, etc.

(H) Tissue pieces→Seedlings
(1) Sterilization

Plant tissues (collected from stems, leaves, etc.) are cut into about 1–10 mm and sterilized in the same manner as in the above procedure (A).

(2) Derivation and multiplication of seedlings

The plant tissue pieces sterilized in the above step (1) are cultured in a 1/5 ANA-MS culture medium (liquid, photoautotrophic culture medium) in which carbon dioxide is enriched to 1%, or in a 1/5 NA-MS culture medium (liquid) containing 0.1–10 µM of a growth control substance, at 20°–25° C. for 30–60 days while shaking at 110–120 rpm/min and illuminating a light of about 1000–3000 lux. As a result, the plant tissue pieces give rise to seedlings. After multiplication for 5–10 weeks, the number of the seedlings (cultigen) can be as many as 100–150 times the number of the plant tissue pieces.

The multiplied seedlings may be stored in the same manner as in the above procedure (A).

This procedure is suitable for the following mosses:
(a) Bryopsida
   Polytrichum, Leucobryum, Dicranum, Hypnum, Sphagnum, etc.
(b) Hepaticopsida
   Haplomitrium, Jungermannia, Metzgeria, etc.

(I) Plant tissue pieces→Calluses→Seedlings (1) Sterilization

The same as in (H).

(2) Derivation of calluses

The plant tissue pieces sterilized in the above step (1) are cultured on a 1/5 AS-MS culture medium (solid) in which the concentration of glucose is controlled to 4–8 weight %, or on an MFS culture medium (solid) at 20°–25° C. for 30–60 days while illuminating a light of about 1500–2000 lux. As a result, the plant tissue pieces give rise to calluses.

(3) Multiplication of calluses

The calluses thus derived can be multiplied and stored in the same manner as in the above procedure (B).

(4) Derivation and multiplication of seedlings

The calluses can be converted to seedlings and multiplied in the same manner as in the above procedure (B). After multiplication for 7–12 weeks, the number of the seedlings (cultigen) can be as many as 100–150 times the number of the plant tissue pieces. The multiplied seedlings may be stored in the same manner as in the above procedure (A).

This procedure is suitable for the following mosses:
(a) Bryopsida
   Atrichum, Polytrichum, Barbula, Sphagnum, etc.
(b) Hepaticopsida
   Plagiochila, Riccia, etc.

(J) Protonemata→Seedlings (1) Sterilization

Protonemata are cut into about 1–10 mm and sterilized in the same manner as in the above procedure (A).

(2) Multiplication of protonemata

The sterilized protonemata are multiplied on a 1/5 NA-MS culture medium (solid) at 20°–25° C. for 5–10 days while illuminating a light of about 1000–3000 lux.

(3) Derivation and multiplication of seedlings

The protonemata thus obtained are cultured in a 1/5 ANA-MS culture medium (liquid, photoautotrophic culture medium) in which carbon dioxide is enriched to 1%, or in a 1/5 NA-MS culture medium (liquid) containing 0.1–10 µM of a growth control substance, at 20°–25° C. for 30–60 days while shaking at 110–120 rpm/min and illuminating a light of about 1000–3000 lux. As a result, the protonemata give rise to seedlings. After multiplication for 6–10 weeks, the number of the seedlings (cultigen) can be as many as 100–150 times the number of the divided protonemata.

The multiplied seedlings may be stored in the same manner as in the above procedure (A).

This procedure is suitable for the following mosses:
(a) Bryopsida
   Ditrichum, Ceratodom, Bartramia, etc.
(b) Hepaticopsida
   Marchantia, Scapania, Jungermannia, etc.

(K) Subterranean stems→Seedlings (1) Sterilization

Subterranean stems are cut into about 1–10 mm and sterilized in the same manner as in the above procedure (A).

(2) Derivation and multiplication of seedlings

The subterranean stems sterilized in the above step (1) are cultured in a 1/5 ANA-MS culture medium (liquid, photoautotrophic culture medium) in which carbon dioxide is enriched to 1%, or in a 1/5 NA-MS culture medium (liquid) containing 0.1–10 µM of a growth control substance, at 20–25° C. for 10–30 days while shaking at 110–120 rpm/min and illuminating a light of about 1000–3000 lux. As a result, the subterranean stems give rise to seedlings. After multiplication for 3–4 weeks, the number of the seedlings (cultigen) can be as many as 100–150 times the number of the divided subterranean stems.

The multiplied seedlings may be stored in the same manner as in the above procedure (A).

This procedure is suitable for the following mosses:
(a) Bryopsida
   Rhodobryum, Hylocomium, Climacium, Pleuroziopsis, etc.

(L) Rhizoids→Seedlings (1) Sterilization

Rhizoids are cut into about 1–10 mm and sterilized in the same manner as in the above procedure (A).

(2) Derivation and multiplication of seedlings

The rhizoids sterilized in the above step (1) are cultured in a 1/5 ANA-MS culture medium (liquid, photoautotrophic culture medium) in which carbon dioxide is enriched to 1%, or in a 1/5 NA-MS culture medium (liquid) containing 0.1–10 µM of a growth control substance, at 20°–25° C. for 10–30 days while shaking at 110–120 rpm/min and illuminating a light of about 1000–3000 lux. As a result, the rhizoids give rise to seedlings. After multiplication for 3–4 weeks, the number of the seedlings (cultigen) can be as many as 100–150 times the number of the divided rhizoids.

The multiplied seedlings may be stored in the same manner as in the above procedure (A).

This procedure is suitable for the following mosses:
(a) Bryopsida
   Racomitrium, Dicranum, Ptilium, Thudium, etc.
(b) Hepaticopsida
   Haplomitrium, Bazzania, Marchantia, etc.

Though the moss seedlings and the method of producing a dense moss mat from these seedlings have been described above together with specific examples of mosses suitable for such applications, it should be noted that the present invention is not limited to them. Any other culture media commonly used for pure culture may be conveniently utilized in the present invention. Also, the formation of calluses can be conducted, if necessary, for the purpose of multiplication and storing. For instance, into the culture method containing no callus-forming step, the callus-forming step may be introduced. In addition to the above-described culture methods, special culture methods may be used. For instance, in the case of Schistostega, the above procedure (D) may be stopped at the stage of multiplication of protonemata, and the multiplied protonemata may preferably be sown as seedlings.

The seedlings obtained in each of the above procedures (A)–(K) may be charged into a culture vessel again to produce the seedlings of the same quality (clones of mosses) repeatedly by pure culture.

[B] Production of dense moss mat

The method of producing a dense moss mat using the seedlings according to the present invention will be explained below.

First, the seedlings obtained by the above procedures are sown onto a nursery. The sowing density may be determined depending on the desired colony density. In general, in the case of a moss garden, the seedlings are sown at a density of about 5–20 per 1 $cm^2$. Also in the case of the dried seedlings, they may be sown directly onto the nursery or after immersion in a water. Further, in a case where the seedlings are kept in a culture medium, they should be washed with water and then sown. Moisture need not be applied under usual conditions, but when the atmosphere and the nursery are dry, water may be preferably supplied onto the nursery by spraying, etc. such that the nursery becomes slightly moist.

The nursery is generally produced from Hyuga soil, Kanuma soil, vermiculite, peat moss, leaf mold, river sand, etc. alone or in combination. Further, foamed perlite (tradename: Aquasoil, etc.), water-absorbing polymers (tradename: Sumikagel, etc.), etc. may be used. In addition, a small amount of charcoal powder may be added. When the sand soil is used for the nursery, the sand soil is preferably sterilized by boiling, baking in an oven, etc.

The sowing of the seedlings may be conducted directly onto a final cultivation place such as a moss garden, a moss pot, etc., but it is preferable that the seedlings are first sown onto a nursery pallet of about 10–30 cm×20–60 cm and then transplanted to the final cultivation place after a relatively dense moss colony is formed. Also, in the case of a large-scale cultivation, the seedlings may be sown directly onto a large cultivation place, or a large number of nursery pallets may be used to cultivate the moss seedlings.

After sowing, the seedlings are cultivated for 150–240 days. For instance, in the case of *Raconitrium canescens*, it forms a relatively dense colony 6 months after the sowing. To obtain a green and healthy moss colony, it is preferable to cultivate the moss in a sunshine while being in contact with the atmosphere. On the other hand, if the moss is used in an application in which appearance is not an important factor (for instance, for sterilization of soil in flower pots or bonsai), the cultivation of the moss grown from the seedlings may be conducted by placing the nursery pallets in plastic greenhouses or casings to avoid the influence of wind and rain. In the latter case, the moss becomes pale green and susceptible to changes of environment, though it can be grown surely and rapidly.

After the moss grows sufficiently, it is transplanted to a final cultivation place such as a moss garden, a moss pot, etc., and kept for 10–15 days so that the moss colony becomes stable on the soil.

Incidentally, in the above cultivation process, when the moss grows non-uniformly to form a moss colony having a non-uniform density, cull-out or transplantation of moss is necessary to make the density of the moss colony uniform.

In the conventional moss-sowing method, it takes about 30–60 days until plumules are formed on moss pieces sown onto the soil, and it is rare that substantially all moss pieces have plumules. In addition, even if substantially all the moss pieces have plumules, the resulting moss colony fails to have a high density. Accordingly, at the initial stage of forming the moss colony, it is very sparse, and one must wait until lateral buds grown from the subterranean stems and the rhizoids propagate sufficiently if the moss colony is to be made uniform. This usually takes 800–1100 days. For instance, in the case of *Dicranum scoparium*, it takes 900–1000 days. This means that it takes an extremely long time until a sufficiently dense moss colony can be obtained by the conventional moss-sowing method.

However, in the present invention, the mosses are purely cultured under the most suitable conditions to produce their seedlings on a large scale in an extremely short period of time. Since the cultured seedlings can surely germinate, a dense moss colony can be formed in a greatly reduced period of time by sowing these cultured seedlings onto a nursery.

In the cultivation method of the present invention, it takes only about 200–300 days until the growing of the moss is completed after the initiation of pure culture, though the time period may vary within the above range depending on the types of the mosses. For instance, in the case of *Dicranum scoparium*, it takes about 210–240 days, which is much shorter than in the conventional moss-sowing method.

Further, in the conventional moss-sowing method, divided leaves and stems of mosses are manually sown one by one onto a nursery. On the other hand, since the seedlings of the present invention are kept in a dry state or in a culture medium, sowing can be completed only by scattering the seedlings at a high density onto a nursery. Therefore, the sowing operation is extremely easy and versatile in the present invention, promising high efficiency.

The present invention will be explained in detail by way of the following Examples without intention of restricting the scope of the present invention thereto.

EXAMPLE 1

The plant bodies of *Dicranum scoparium* were collected, and only gametophores were separated out, cut to about 5 mm by a scissors and sterilized. Each one of the cut gametophores was cultured on a 1/5 NA-MS culture medium (solidified with 8% agar) at 25° C. while illuminating a light of 2000 lux. After removing portions infected with fungi, etc., the culture operation of the gametophores were repeated 5 times to produce sterilized gametophores.

The sterilized gametophores were then charged together with 1 µM of kinetin (growth control substance) into a flask containing a 1/5 ANA-MS culture medium (liquid) in which carbon dioxide was enriched to 1%, and the flask was set in a shaking machine. The culture of the gametophores was conducted at 25° C. for 7 days while shaking at 110 rpm/min and illuminating a light of 2000 lux, so that the gametophores were differentiated to form seedlings.

The seedlings thus cultured were removed from the flask, fully washed with the 1/5 NA-MS culture medium, and then introduced into the 1/5 NA-MS culture medium containing no growth control substance to continue the culture of the seedlings under the same conditions for 6 weeks. As a result, about 100 times as many seedlings as the original cut and sterilized gametophores were obtained. The seedlings were fully washed with sterilized distilled water to completely remove the culture medium, and then dried at 30° C. while blowing the air. Thus, the moss seedlings were obtained in a dry state.

The seedlings were sown at a density of about 5 per 1 $cm^2$ onto a nursery pallet of 30 cm×60 cm×3 cm filled with sand in a thickness of 1 cm, and then cultivated in an open place.

After 180 days, the *Dicranum scoparium* formed a dense moss colony, which could be transplanted to a final cultivation place such as a moss garden.

Comparative Example 1

A colony of *Dicranum scoparium* was manually separated to individual stems, and they were sown onto a nursery at a density of 30×30 per a pallet in the same manner as in Example 1.

The *Dicranum scoparium* grew extremely slowly as compared with those in Example 1, and the resulting moss colony was still sparse after 180 days, failing to be transplanted to a final cultivation place.

EXAMPLE 2

Sporophytes of *Pyrrhobryum dozyanum* were collected, and only capsules were separated out with calyptrae removed to obtain spores. The spores were cultured on a 1/5 NA-MS culture medium (solidified with 8% agar) at 25° C. while illuminating a light of 2000 lux. After-removing portions infected with fungi, etc., the culture operation of the gametophores was repeated 5 times to produce sterilized spores.

The sterilized spores were then cultured on a 1/5 NA-MS culture medium (solidified with 8% agar) at 25° C. for 14 days while illuminating a light of 2000 lux. As a result, protonemata were obtained.

The protonemata were charged together with 1 μM of kinetin (growth control substance) into a flask containing a 1/5 ANA-MS culture medium (liquid) in which carbon dioxide was enriched to 1%, and the flask was set in a shaking machine. The culture of the protonemata was conducted at 25° C. for 7 days while shaking at 110 rpm/min and illuminating a light of 2000 lux, so that the protonemata were differentiated to form seedlings.

The seedlings thus cultured were removed from the flask, fully washed with the 1/5 NA-MS culture medium, and then introduced into the 1/5 NA-MS culture medium containing no growth control substance to continue the culture of the seedlings under the same conditions for 50 days. The seedlings were fully washed with a sterilized distilled water to completely remove the culture medium, and then dried at 30° C. while blowing the air. Thus, the moss seedlings were obtained in a dry state.

The seedlings were sown at a density of about 5 per 1 cm$^2$ onto a nursery pallet of 30 cm×60 cm×3 cm filled with sand in a thickness of 1 cm, and then cultivated in an open place.

After 180 days, the *Pyrrhobryum dozyanum* formed a dense moss colony, which could be transplanted to a final cultivation place such as a moss garden.

EXAMPLE 3

Sporophytes of *Barbula unguiculata* were collected, and only capsules were separated out and sterilized with calyptrae removed to obtain spores. The spores were cultured on a 1/5 NA-MS culture medium (solidified with 8% agar) at 25° C. while illuminating with a light of 2000 lux. After removing portions infected with fungi, etc., the culture operation of the gametophores was repeated 5 times to produce sterilized spores.

The sterilized spores were then cultured on a 1/5 NA-MS culture medium (solid) at 25° C. for 14 days while illuminating with a light of 2000 lux. As a result, protonemata were obtained.

The protonemata were cultured on a 1/5 AS-MS culture medium (solid) in which the concentration of glucose was controlled to 4 weight % at 25° C. for 50 days while illuminating with a light of 1500 lux. As a result, calluses were obtained.

The calluses were charged together with 1 μM of kinetin (growth control substance) into a flask containing a 1/5 ANA-MS culture medium in which carbon dioxide was enriched to 1%, and the flask was set in a shaking machine. The culture of the calluses was conducted at 25° C. for 50 days while shaking at 110 rpm/min and illuminating with a light of 2000 lux, so that the calluses were differentiated to form seedlings.

The seedlings thus cultured were removed from the flask, fully washed with the 1/5 NA-MS culture medium, and then introduced into the 1/5 NA-MS culture medium containing no growth control substance to continue the culture of the seedlings under the same conditions for 50 days. The seedlings were fully washed with sterilized distilled water to completely remove the culture medium, and then dried at 30° C. while blowing air. Thus, the moss seedlings were obtained in a dry state.

The seedlings were sown at a density of about 5 per 1 cm$^2$ onto a nursery pallet of 30 cm×60 cm×3 cm filled with sand in a thickness of 1 cm, and then cultivated in an open place.

After 180 days, the *Barbula unguiculata* formed a dense moss colony, which could be transplanted to a final cultivation place such as a moss garden.

As described in detail, since plant tissues of mosses such as gametophores, calluses, protonemata, etc. are purely cultured in the present invention, they can be multiplied on a large scale in a culture tank to produce seedlings corresponding to plumules in a short period of time. The seedlings (cultigen) may be sown onto a nursery to form a dense moss colony. By this procedure, the dense moss colony can be easily produced in a greatly reduced period of time as compared with the conventional methods.

Also, according to the cultivation method of the present invention, the seedlings corresponding to plumules can be sown at a desired density, so that manual operations which are inevitable in the conventional methods can be eliminated.

The method of the present invention makes it possible to produce dense moss mats of various mosses at a high density in a short period of time.

What is claimed is:

1. A method for producing a dense mat of moss comprising:
   (a) culturing pure plant tissues of said moss in a culture medium to generate seedlings of said plant tissues;
   (b) sowing said seedlings onto a nursery at a density of about 5–20 seedlings per cm$^2$; and
   (c) nurturing said seedlings until maturity.

2. The method according to claim 1 wherein said plant tissues are selected from the group consisting of cut tissue pieces, gametophores, calluses, protonemata, spores, gemma, subterranean stems and rhizoids.

3. The method according to claim 1 wherein said seedlings are dried after step (a) by a method selected from the group consisting of air drying at 25°–35° C., drying under sunshine, and freeze-drying at a temperature between −20° and −5° C.

* * * * *